(12) United States Patent
Schooley et al.

(10) Patent No.: US 6,521,459 B1
(45) Date of Patent: Feb. 18, 2003

(54) METHOD AND APPARATUS FOR TESTING THE ACIDITY OF A LUBRICANT IN A CLIMATE CONTROL SYSTEM

(75) Inventors: Donald L. Schooley, Grove City, OH (US); Richard C. Cavestri, Columbus, OH (US); Don Richard Nemeth, Setmer, FL (US)

(73) Assignee: Bright Solutions, Inc., Troy, MI (US)

( * ) Notice: Subject to any disclaimer, the term of this patent is extended or adjusted under 35 U.S.C. 154(b) by 0 days.

(21) Appl. No.: 09/551,560

(22) Filed: Apr. 18, 2000

(51) Int. Cl.[7] ................................................ G01N 33/26
(52) U.S. Cl. ............................ 436/61; 436/3; 436/143; 436/164; 436/166; 422/61
(58) Field of Search ............................. 422/61; 436/61, 436/3, 143, 164, 166

(56) References Cited

U.S. PATENT DOCUMENTS

| 2,953,439 | A | * | 9/1960 | Elliot et al. .................... 436/61 |
| 4,288,402 | A | * | 9/1981 | Ellis ............................. 422/61 |
| 4,654,309 | A | * | 3/1987 | Mlinar et al. .................. 436/61 |
| 5,304,576 | A | * | 4/1994 | Martinez ....................... 521/41 |
| 5,707,871 | A | | 1/1998 | Sadhir et al. ................. 436/61 |
| 6,174,731 | B1 | * | 1/2001 | Strochkova et al. ........ 436/163 |

FOREIGN PATENT DOCUMENTS

RU          2109280       *   4/1998

OTHER PUBLICATIONS

Mesitylene, Material Safety Data Sheet, Nov. 2001.*

* cited by examiner

*Primary Examiner*—Jill Warden
*Assistant Examiner*—La Toya I. Cross

(57) ABSTRACT

A test kit for testing acidity of a lubricant in a climate control system containing a naphthalimide dye contains an aqueous solution having a salt and a known amount of hydroxide and an organic solution containing an alcohol and an organic solvent having a flash point of at least 130° F. When a lubricant is added to a combination of the aqueous solution and the organic solution, the color of the bottom layer indicates the acid content of the lubricant.

20 Claims, No Drawings

METHOD AND APPARATUS FOR TESTING THE ACIDITY OF A LUBRICANT IN A CLIMATE CONTROL SYSTEM

BACKGROUND OF THE INVENTION

This invention relates to test kits for detecting acidity in a lubricant of a climate control system which may contain a leak detection dye.

In climate control systems, such as heating, cooling, ventilating, and air conditioning systems, lubricants oils are tested for acidity as an indication of suitability for continued use and as a means for detecting contamination of the climate control system. Acid test kits for use with climate control systems can show whether or not the acidity of the lubricant is low enough to continue using the lubricant in the system. The test kit can show a useable range of acid content (acid number) in the lubricant, a range where the user should be aware that lubricant replacement may be suggested, and a range where the climate control system should not be used until the lubricant is replaced.

Colored lubricants are becoming more common due to the use of a leak detection dye, such as a naphthalimide dye, in climate control systems, which can make it more difficult to accurately determine the acid content of the lubricant. For example, some acidity tests, such as ASTM D974-64, are not easy to use in the field and may not perform well with highly colored lubricants because the color changes that are produced by in the test can be obscured by the color of the sample.

SUMMARY OF THE INVENTION

In general, the invention features a test kit for determining the acid content of a lubricant in a climate control system. The lubricant can contain a leak detection dye, such as a naphthalimide dye. The test kit contains an aqueous solution having a salt and a known amount of hydroxide and an organic solution containing an alcohol and an organic solvent having a flash point of at least 130° F., preferably 150° F. or higher. When a lubricant is added to a combination of the aqueous solution and the organic solution, the mixture separates into a bottom layer and an upper layer. The color of the bottom layer clearly indicates the acid content of the lubricant and reliably provides the range of acid content of the lubricant. The indicator colors are distinct from the color of the lubricant, for example, the color of the leak detection dye, and do not cause confusion with the color of the lubricant.

In one aspect, the invention features an acid test kit for determining the acidity of a lubricant from a climate control system. The kit includes an aqueous solution including water, a salt, and a hydroxide and an organic solution including a pH indicator, 2-propanol, and an organic solvent having a flash point of at least 130° F.

In another aspect, the invention features a process of manufacturing an acid test kit for determining acidity of a lubricant from a climate control system. The method includes dissolving a salt in a known volume of water and adding a volume of a hydroxide solution having a known concentration to form an aqueous solution; and dissolving a pH indicator in a mixture of 2-propanol and an organic solvent having a flash point of at least 130° F. The volume of hydroxide solution added to the water and salt can form an aqueous solution having a concentration of 0.001 to 0.00001 M, depending on a threshold acid content selected for detection.

In another aspect, the invention features a method for testing the acid content of a lubricant from a climate control system. The method includes obtaining a lubricant from a climate control system, combining a first amount of the lubricant with a second volume of an organic solution including a pH indicator, 2-propanol, and an organic solvent having a flash point of at least 130° F. and a third volume of an aqueous solution including water, a salt, and a hydroxide to form a mixture, shaking the mixture, and observing a color of a bottom layer of the mixture to determine the acid content of the lubricant. The ratio (g:mL:mL) of the first amount to the second volume to the third volume can be 6.2:9.0:8.5.

The threshold acid content of the lubricant can be between 0.05 and 0.5 total acid number (TAN), preferably 0.1 or 0.2 TAN. The threshold acid content can vary for different lubricants. The color of the bottom layer indicates the TAN of the lubricant. TAN is calculated as the quantity of base, expressed in milligrams of potassium hydroxide, that is required to titrate all acidic materials in a 1 gram sample of the lubricant that have a pKa sufficient to react with the hydroxide. For example, the color of the bottom layer is a first color when the acid content of the lubricant is 0.02 TAN or less, a second color if the acid content of the lubricant is 0.02 to 0.08 TAN, or a third color if the acid content of the lubricant is 0.1 TAN or greater. The first color can be blue, the second color can be green and the third color can be yellow.

The organic solvent is an aromatic- or aliphatic-containing hydrocarbon solvent that is free of acidic groups, such as carboxyl or hydroxyl groups, or basic groups, such as amino groups. In order to reduce the flammability of the organic solution, the organic solvent has a relatively high flash point of at least 130° F., preferably at least 150° F. Flash point is the temperature at which a liquid gives off a vapor sufficient to form an ignitable mixture with air near the surface of the liquid. By including an organic solvent having a relatively high flash point, the acid test kit can be less hazardous to use in the field. The organic solvent is essentially chemically inert. The organic solvent can be, for example, CHEVRON ion exchange solvent (available from Standard Oil of California) having a flash point of 195° F., ESCAID 100™ and ESCAID 110™ (available from Exxon-Europe, essentially a petroleum distillate) having a flash point of 180° F., NORPAR® 12 (available from Exxon-USA, essentially a petroleum distillate) with a flash point of 160° F., CONOCO C1214 (available from Conoco) with a flash point of 160° F., AROMATIC 150™ (an aromatic kerosene available from Exxon-USA) having a flash point of 150° F., and AROMATIC 200™ (an aromatic kerosene available from Exxon-USA) having a flash point of 217° F., and other commercially available kerosene and petroleum fractions. More particularly, AROMATIC 150™ is a high purity aromatic mixture of about 8% C9 aromatic compounds, about 74% C10 aromatic compounds, about 15% C11 aromatic compounds, and about 1% C12 aromatic compounds, and about 1% of nonaromatic compounds. Preferably, the organic solvent can be AROMATIC 150™ or AROMATIC 2000™.

The test kit is a two-phase type wherein the phases separate rapidly. The separation can occur within 10 minutes, preferably within 5 minutes, more preferably within 3 minutes, and most preferably within one minute. The high ionic strength of the aqueous solution facilitates rapid separation without emulsification.

The aqueous solution can be free of alcohol. The organic solution can be free of ethanol. When the aqueous solution and organic solution are both free of ethanol, the color of the indicator is more brilliant that when the solutions include ethanol.

Additional features and advantages of the invention will become apparent from the detailed description of the invention.

DETAILED DESCRIPTION

The acid test kit is used to determine the fitness of a lubricant, such as a polyolester lubricant, a polyvinyl ether, mineral oil, or alkyl benzene, used in a climate control system. The acid test kit can be used to rapidly determine excess acid content in lubricants due to a partial breakdown of the lubricant into organic acids. An acid content above a threshold value indicates that the lubricant has broken down to such an extent as to render it unfit for further use within the compressor.

The climate control system can be a heating, ventilating, refrigeration, or air conditioning system. The air conditioning system can be an automotive, portable, residential, or commercial air conditioning system. Once assembled, the air conditioning system can be charged with a refrigerant, a lubricant, and, optionally, a leak detection dye. For example, the lubricant can include a leak detection dye, such as a naphthalimide dye or other emissive dye. The leak detection dye can be soluble in the refrigerant, the lubricant, or the refrigerant-lubricant mixture. The dye content of the system can be below about 0.1 percent. Dye circulates throughout the system and can show the presence of a leak by a colored visual indication, such as fluorescence or other emission, which can be detected after excitation with light from a light source having a light emission wavelength from 190 nanometers to 700 nanometers. The presence of a leak can be determined by the presence of an emission. The presence of the dye gives the lubricant a color, which can interfere with determining the acid content of the lubricant using ordinary indicator systems.

The refrigerant can include chlorofluorocarbons, hydrochlorofluorocarbons, hydrofluorocarbons, carbon dioxide, ammonia, halogenated or ether derivatives of methane or ethane, or halogenated ether or cyclic derivatives of propane, butane, pentane, or other natural or synthetic hydrocarbons.

Suitable lubricants include natural mineral oils, refined mineral oils, synthetic hydrocarbons (SHC), alkylbenzenes (AB), polyalphaolefins (PAO), polyvinyl ethers, synthetic polyalkylene glycols (PAG) that are terminated as monoethers, diethers, esters, or a general class of polyol ester (POE) lubricants including either di-, tri-, tetra- or polyfunctional pentaerythritol esters. Particular lubricants suitable for testing include, for example, EMERY 2927a™, MOBIL ARCTIC EAL 68™ (essentially a polyester), MOBIL RL22H™, WITCO IGS™ (essentially a mineral oil), ZEROL 150™ (essentially a alkyl benzene), UCON 488, FORD PAG, CHRYSLER PAG or any other automotive PAG and POE lubricants.

The test kit uses a pH indicator that changes color in particular pH ranges. When the lubricant is colored with a leak detection dye, particularly a naphthalimide dye, an acid test kit including an aqueous solution containing water, a salt, and a hydroxide and an organic solution including a pH indicator, 2-propanol, and an organic solvent having a flash point of at least 130° F. accurately and safely provides the acid content of the lubricant. The relatively high flash point of the organic solvent decreases the flammability of the organic solution. The salt is a water-soluble inorganic salt, such as sodium chloride, calcium chloride, magnesium chloride, sodium bromide, and like materials; sodium chloride is preferred. The organic solution can include 30 to 50 volume % 2-propanol and 70 to 50 volume % Aromatic 150. The pH indicator can be thymol blue. The aqueous solution can include between 8 and 12 weight % salt and 0.001 M and 0.00001 M hydroxide.

In the acid test kit, the organic solvent can also oxidize in air, leading to formation of acids in the organic solution. This can be slowed down or prevented by adding an antioxidant to the organic phase, such as butylated hydroxytoluene (BHT).

The acid test kit is prepared by dissolving a salt in a known volume of water and adding a volume of a hydroxide solution having a known concentration to form an aqueous solution and dissolving a pH indicator in a mixture of 2-propanol and an organic solvent having a flash point of at least 130° F. The hydroxide solution can be a solution formed from potassium hydroxide, sodium hydroxide, or lithium hydroxide; potassium hydroxide is preferred. The hydroxide solution can have a hydroxide concentration of 1.0 M or 0.1 M. The method of preparing the acid test kit is simple, without requiring pH measurement during the preparation.

The method for testing the acid content of a lubricant from a climate control system using the acid test kit rapidly determines the acid content of the lubricant. A first amount of the lubricant is withdrawn from the climate control system. The first amount of lubricant is combined with a second volume of the organic solution and a third volume of the aqueous solution in a vessel. The mixture in the vessel is shaken. The aqueous and organic phases then separate in the vessel to form a top layer and a bottom layer. The color of the bottom layer of the mixture is observed to determine the acid content of the lubricant. When the aqueous solution includes 0.00075 M hydroxide, the color is a first color when the acid content of the lubricant is 0.02 TAN or less, a second color if the acid content of the lubricant is 0.02 TAN to 0.08 TAN, or a third color if the acid content of the lubricant is 0.1 TAN or greater.

The hydroxide content of the aqueous layer is selected to provide indicator color changes based on the pH of the solution after the lubricant, the organic solution and the aqueous solution are combined. If the color of the bottom layer is blue to blue-green, the lubricant is satisfactory for further use in the climate control system. If the color of the bottom layer is green to yellow-green, the lubricant is marginally qualified for further use in the climate control system. If the color of the bottom layer is yellow, the lubricant contains too much acid and should be changed.

In an example, an acid field test kit containing an aqueous solution and organic solution was made according to the following procedure. To prepare the aqueous solution, distilled water was poured into a beaker, NaCl was added, and the mixture was stirred until the salt dissolved. A fixed volume of KOH solution was added to the salt solutions and stirred until thoroughly mixed. It is important not to stir the solution excessively after KOH addition. The aqueous solution was bottled and immediately purged with nitrogen.

To prepare the organic solution, thymol blue powder was added to 2-propanol and stirred for at least 15 minutes. The solution was red. The thymol blue may not all dissolve. The AROMATIC 150™ was added. The organic solution was bottled. The 2-propanol/AROMATIC 150™ solution was saturated with thymol blue. The organic mixture was not filtered before bottling. The solution was decanted from the undissolved crystals.

The composition is shown in Table I.

TABLE 1

| Component | Example 1 |
|---|---|
| Aqueous Solution | |
| Distilled water | 339 mL |
| NaCl | 40 g |
| KOH (0.1 N; aqueous) | 2.57 mL |
| Organic Solution | |
| 2-Propanol | 904 mL |
| AROMATIC 150 ™ | 1340 mL |
| Thymol Blue | 0.05 g |

To test the acid content of lubricant, 6.2 g lubricant was mixed with 9.0 mL of the organic solution, and 8.5 mL of the aqueous solution. Multiples of these three ingredients, keeping the ratios of the three components constant, give the same result. The following lubricants were tested: a polyolester MOBIL RL22H™; a mineral oil WITCO IGS™; and an alkyl benzene ZEROL 150™. And some lubricant samples included a naphthalimide dye (1, 2, and 4% w/w dye in oil). The mixture was shaken and the aqueous and organic layers were allowed to separate. The lubricant at acid content of 0.02 TAN or less produced a blue bottom layer, the lubricant at 0.02 to 0.08 TAN acid content produced a lime green bottom layer, and the lubricant at 0.1 TAN or greater acid content produced a yellow bottom layers. The indicator colors were brighter when using the solution of Example 1, which was free of ethanol, than a comparative example including ethanol.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An acid test kit for determining the acidity of a lubricant from a climate control system comprising:
    an aqueous solution including water, a salt, and a hydroxide; and
    an organic solution including a pH indicator, 2-propanol, and an organic solvent having a flash point of at least 130° F.

2. The acid test kit of claim 1, wherein the pH indicator is thymol blue.

3. The acid test kit of claim 1, wherein the aqueous solution is free of alcohol.

4. The acid test kit of claim 3, wherein the organic solution is free of ethanol.

5. The acid test kit of claim 1, wherein the organic solvent is AROMATIC 150™.

6. The acid test kit of claim 4, wherein the organic solvent is AROMATIC 150™.

7. The acid test kit of claim 1, wherein the aqueous solution includes between 8 and 12 weight % salt and 0.001 M to 0.00001 M hydroxide.

8. The acid test kit of claim 7, wherein the salt is selected from the group consisting of sodium chloride, calcium chloride, magnesium chloride, and sodium bromide.

9. The acid test kit of claim 7, wherein the organic solution includes 30 to 50 volume % 2-propanol and 70 to 50 volume % AROMATIC 150™.

10. A process of manufacturing an acid test kit for determining acidity of a lubricant from a climate control system comprising:
    dissolving a salt in a known volume of water and adding a volume of a hydroxide solution having a known concentration to form an aqueous solution; and
    dissolving a pH indicator in a mixture of 2-propanol and an organic solvent having a flash point of at least 130° F.

11. The method of claim 10, wherein the indicator is thymol blue.

12. The method of claim 11, wherein the aqueous solution is free of alcohol.

13. The method of claim 12, wherein the organic solution is free of ethanol.

14. The method of claim 10, wherein the organic solvent is AROMATIC 150™.

15. The method of claim 13, wherein the organic solvent is AROMATIC 150™.

16. The method of claim 15, wherein the volume of hydroxide solution added to the water and salt forms the aqueous solution having a concentration of 0.001 M to 0.00001 M hydroxide.

17. The method of claim 16, wherein the organic solution includes 30 to 50 volume % 2-propanol and 70 to 50 volume % AROMATIC 150™.

18. An acid test kit for determining the acidity of a lubricant from a climate control system comprising:
    an aqueous solution, the aqueous solution being free of alcohol; and
    an organic solution including a pH indicator, 2-propanol and AROMATIC 150™, the organic solution being free of ethanol.

19. The acid test kit of claim 18, wherein the aqueous solution includes between 8 and 12 weight % salt and 0.001 M to 0.00001 M hydroxide.

20. The acid test kit of claim 18, wherein the organic solution includes 30 to 50 volume % 2-propanol and 70 to 50 volume % AROMATIC 150™.

* * * * *